US005856099A

United States Patent [19]
Miraglia et al.

[11] Patent Number: 5,856,099
[45] Date of Patent: Jan. 5, 1999

[54] ANTISENSE COMPOSITIONS AND METHODS FOR MODULATING TYPE I INTERLEUKIN-1 RECEPTOR EXPRESSION

[75] Inventors: Loren Miraglia, Encinitas; C. Frank Bennett, Carlsbad; Nicholas Dean, Encinitas, all of Calif.; Thomas Geiger, Freiburg, Germany

[73] Assignee: Isis Pharmaceuticals, Inc., Carlsbad, Calif.

[21] Appl. No.: 651,692

[22] Filed: May 21, 1996

[51] Int. Cl.$^6$ .............................. C12Q 1/68; A61K 48/00; C07H 71/04; C12N 15/86
[52] U.S. Cl. .............................. 435/6; 435/91.1; 435/325; 435/366; 514/44; 536/23.1; 536/24.3; 536/24.5
[58] Field of Search .............................. 514/44; 536/23.1, 536/24.5, 25.3, 24.3; 436/94; 435/6, 91.1, 325, 366

[56] References Cited

U.S. PATENT DOCUMENTS

| | | | |
|---|---|---|---|
| 4,689,320 | 8/1987 | Kaji | 514/44 |
| 4,806,463 | 2/1989 | Goodchild et al. | 435/5 |
| 5,013,830 | 5/1991 | Ohtsuka et al. | 536/27 |
| 5,087,617 | 2/1992 | Smith | 514/44 |
| 5,098,890 | 3/1992 | Gewirtz et al. | 514/44 |
| 5,135,917 | 8/1992 | Burch | 514/44 |
| 5,138,045 | 8/1992 | Cook et al. | 536/27 |
| 5,166,195 | 11/1992 | Ecker | 514/44 |
| 5,194,428 | 3/1993 | Agrawal et al. | 514/44 |
| 5,223,618 | 6/1993 | Cook et al. | 544/276 |
| 5,242,906 | 9/1993 | Pagano et al. | 514/44 |
| 5,264,423 | 11/1993 | Cohen et al. | 514/44 |
| 5,276,019 | 1/1994 | Cohen et al. | 514/44 |
| 5,378,825 | 1/1995 | Cook et al. | 536/25.34 |
| 5,585,479 | 12/1996 | Hoke et al. | 536/24.5 |

FOREIGN PATENT DOCUMENTS

| | | |
|---|---|---|
| 339842 | 4/1989 | European Pat. Off. . |
| 399330 | 5/1990 | European Pat. Off. . |
| 91/06556 | 5/1991 | WIPO . |
| 91/10671 | 7/1991 | WIPO . |
| 91/15499 | 10/1991 | WIPO . |
| 92/02258 | 2/1992 | WIPO . |
| 92/03568 | 3/1992 | WIPO . |
| 94/00467 | 1/1994 | WIPO . |

OTHER PUBLICATIONS

Rojanasakul, Antisense oligonucleotide therapeutics: drug delivery and targeting, Advanced Drug Delivery Reviews, vol. 18, pp. 115–131, 1996.

Miller et al., Gene transfer and antisense nucleic acid techniques, Parasitology Today, vol. 10(3), pp. 92–97, 1994.

Gura, Antisense has growing pains, Science, vol. 270, pp. 575–577, Oct. 1995.

Wu–Pong, Oligonucleotides: opportunities for drug therapy and research, Pharmaceutical Technology, vol. 18, pp. 102–114, Oct. 1994.

Stull et al, Antigene, ribozyme, and aptamer nucleic acid drugs: progress and prospects, Pharmaceutical Research, vol. 12(4), pp. 465–483, 1995.

Wagner, Gene inhibition using antisense oligonucleotides, Nature, vol. 372, pp. 333–335, Nov. 1994.

Stein et al., Antisense oligonucleotides as therapeutic agents—Is the bullet realy magical?, Science, vol. 261, pp. 1004–1012, Aug. 1993.

Weiss, Upping the antisense ante, Science News, vol. 139, pp. 108–109, 1991.

Milligan et al., Current concepts in antisense drug design, J. Med. Chem., vol. 36(14), pp. 1923–1937, Jul. 1993.

Burch et al., Oligonucleotides antisense to the interleukin 1 receptor mRNA block the effects of interleukin 1 in cultured murine and human fibroblasts and in mice, J. Clin. Investi., vol. 88, pp. 1190–1196, Oct. 1991.

Monia et al., Evaluation of 2'–modified oligonucleotides containing 2'–deoxy gaps as antisense inhibitors of gene expression, J. Biol. Chem., vol. 268(19), pp. 14514–14522, Jul. 1993.

Sims et al., Cloning the interleukin 1 receptor from human T cells, Proc. Natl. Acad. Sci., vol. 86, pp. 8946–8950, Nov. 1989.

Arend, "Interleukin–1 Receptor Antagonist", *Adv. Immunol.*, 54, 167 (1993).

Chiang et al., "Antisense Oligonucleotides Inhibit Intercellular Adhesion Molecule 1 Expression by Two Distinct Mechanisms", *J. Biol. Chem.*, 266, 18162 (1991).

Dayer and Burger, "Interleukin–1, tumor necrosis factor and their specific inhibitors", *Eur. Cytokine Netw.*, 5, 563 (1994).

Dean et al., "Inhibitor of Protein Kinase C–α Expression in Human A549 Cells by Antisense Oligonucleotides Inhibits Induction of Intercellular Adhesion Molecule 1 (ICAM–1) mRNA by Phorbol Esters", *J. Biol. Chem.*, 269, 16416 (1994).

Dean and McKay, "Inhibition of protein kinase C–α expression in mice after systemic administration of phosphorothioate antisense oligodeoxynucleotides", *Proc. Natl. Acad. Sci.*, 91, 11762 (1994).

Dinarello, "The biological properties of interleukin–1", *Eur. Cytokine Netw.*, 5, 517 (1994).

Dinarello, "The Interleukin–1 family: 10 years of discovery", *The FASEB Journal*, 8, 1314 (1994).

Dinarello, "Blocking Interleukin–1 in Disease", *Blood Purif.*, 11, 118 (1993).

(List continued on next page.)

*Primary Examiner*—John L. LeGuyader
*Assistant Examiner*—Andrew Wang
*Attorney, Agent, or Firm*—Law Offices of Jane Massey Licata

[57] ABSTRACT

Compositions and methods are provided for the treatment and diagnosis of diseases amenable to treatment through modulation of type I IL-1 receptor mRNA expression. In accordance with preferred embodiments, oligomers are provided which are specifically hybridizable with DNA or RNA encoding type I interleukin-1 receptor. Methods of modulating type I IL-1 receptor expression and of treating animals suffering from diseases amenable to therapeutic intervention by modulating the expression of type I interleukin-1 receptor with an oligomer specifically hybridizable with DNA or RNA encoding type I interleukin-1 receptor are disclosed.

29 Claims, 6 Drawing Sheets

OTHER PUBLICATIONS

Colota et al., "Interleukin–1 Type II Receptor: A Decoy Target for IL–1 That Is Regulated by IL–4", *Science*, 261, 472 (1993).

Dinarello and Thompson, "Blocking IL–1: interleukin 1 receptor antagonist in vivo and in vitro," *Immunol. Today*, 12, 404 (1991).

Dinarello and Wolff, "The Role of Interleukin–1 in Disease", *N. Engl. J. Med.*, 328, 106 (1993).

Eckstein et al., "Polynucleotides Containing 2'–Chloro–2'–deoxyribose", *Biochemistry*, 11, 4336 (1972).

Geiger et al., "Neutralization of interleukin–1β activity in vivo with a monoclonal antibody alleviates collagen–induced arthritis in DBA/1 mice and prevents the associate acute–phase response", *Clin Exp. Rheumatol.*, 11, 515 (1993).

Guschlbauer and Jankowski, "Nucleoside conformation is determined by the electronegativity of the sugar substitute", *Nucleic Acids Res.*, 8, 1421 (1980).

Ikehara et al., "Recognition by restriction endonuclease EcoRI of deoxyoctanucleotides containing modified sugar moieties", *Eur. J. Biochem.*, 139, 447 (1984).

Ikehara et al., "Polynucleotides. L. Synthesis and properties of poly (2'–chloro–2'–deoxyadenylic acid) and poly(2'–bromo–2'–deoxyadenylic acid)", *Nucleic Acids Res.*, 4, 4249 (1978).

Inoue et al., "Synthesis and hybridization studies on two complementary nona (2'–O–methyl ribonucleotides", *Nucleic Acids Research*, 15, 6131 (1987).

McNamara et al., "Interleukin–1 Receptor Antibody (IL–l-rab) Protection and Treatment against Lethal Endotoxemia in Mice", *J. Surgical Res.*, 54, 316 (1993).

Rychlik and Rhoads, , "A computer program for choosing optimal oligonucleotides for filter hybridization, sequencing and in vitro amplification of DNA", *Nucleic Acids Res.*, 17, 8543 (1989).

Sambrook et al., *Molecular Cloning. A Laboratory Manual*, Cold Spring Harbor Laboratory Press, 1989, vol. 2, pp. 10.59 and 11.31–11.32.

Schotanus et al., "Human Recombinant Interleukin–1 Receptor Antagonist Prevents Adrenocorticotropin, but not Interleukin–6 Responses to Bacterial Endotoxin in Rats", *Endocrinology*, 133, 2461 (1994).

Shibahara et al., "Inhibition of human immunodeficiency virus (HIV–1 replication of synthetic oligo–RNA derivatives", *Nucleic Acids Research*, 17, 239 (1987).

Sims et al., "The Two Interleukin–1 Receptors Play Different Roles in IL–1 Actions", *Clin. Immunol. Immunopath.*, 72, 9 (1994).

Sims and Dower, "Interleukin–1 receptors", *Eur. Cytokine Netw.*, 5, 539 (1994).

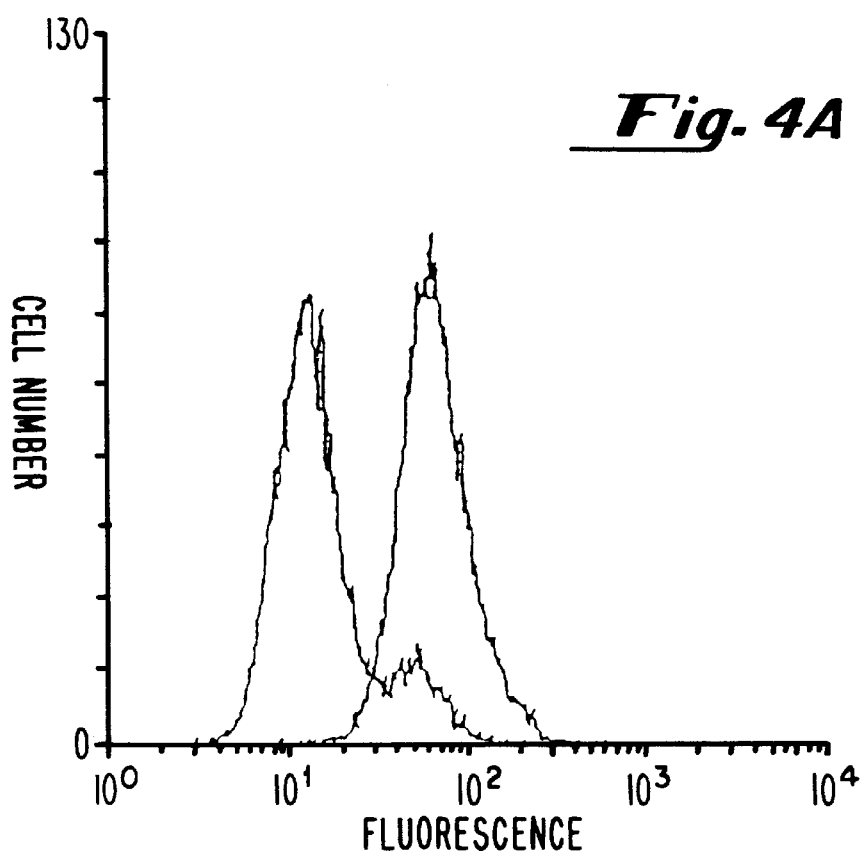
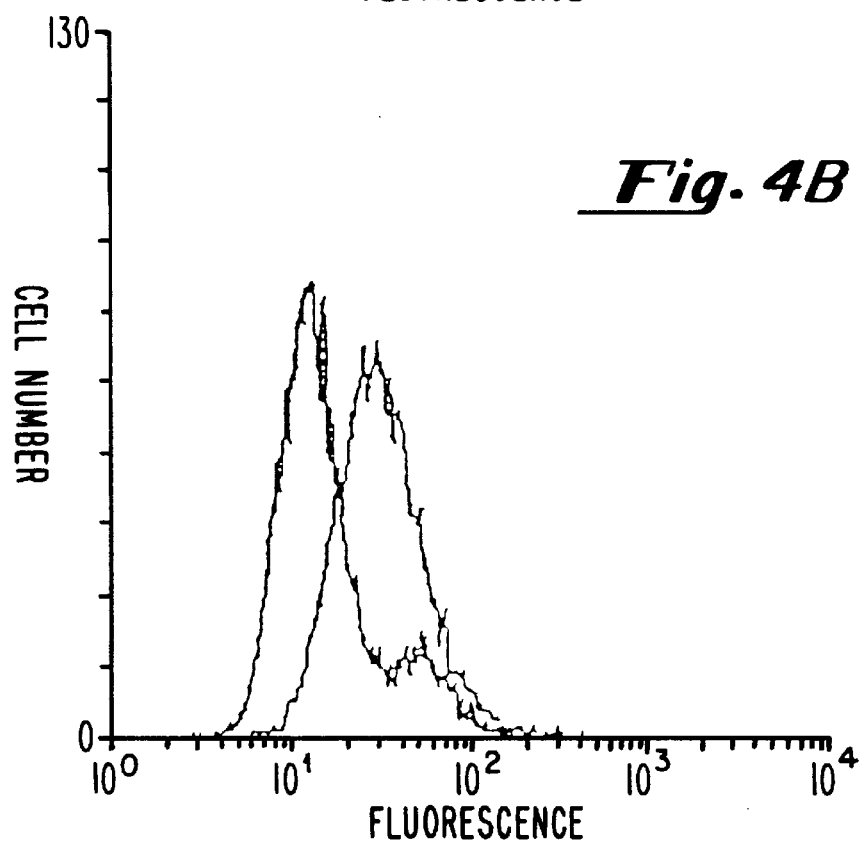

SEQUENCE LISTING ( 1 ) GENERAL INFORMATION:

( i i i ) NUMBER OF SEQUENCES: 42

( 2 ) INFORMATION FOR SEQ ID NO:1:

( i ) SEQUENCE CHARACTERISTICS:
        ( A ) LENGTH: 20
        ( B ) TYPE: Nucleic Acid
        ( C ) STRANDEDNESS: Single
        ( D ) TOPOLOGY: Linear ( i v ) ANTI-SENSE: Yes ( x i ) SEQUENCE DESCRIPTION: SEQ ID NO: 1:

C C T C C A G G G C     T G C G G C G G C T                         2 0

( 2 ) INFORMATION FOR SEQ ID NO:2:

( i ) SEQUENCE CHARACTERISTICS:
        ( A ) LENGTH: 20
        ( B ) TYPE: Nucleic Acid ( C ) STRANDEDNESS: Single
( D ) TOPOLOGY: Linear ( i v ) ANTI-SENSE: Yes ( x i ) SEQUENCE DESCRIPTION: SEQ ID NO: 2:

AGGGCTGCGG CGGCTCCACT                                    20

( 2 ) INFORMATION FOR SEQ ID NO:3:

( i ) SEQUENCE CHARACTERISTICS:
( A ) LENGTH: 20
( B ) TYPE: Nucleic Acid
( C ) STRANDEDNESS: Single
( D ) TOPOLOGY: Linear ( i v ) ANTI-SENSE: Yes ( x i ) SEQUENCE DESCRIPTION: SEQ ID NO: 3:

CACCGAGGAG CAGGCGCGGC                                    20

( 2 ) INFORMATION FOR SEQ ID NO: 4:

( i ) SEQUENCE CHARACTERISTICS:
( A ) LENGTH: 20
( B ) TYPE: Nucleic Acid
( C ) STRANDEDNESS: Single
( D ) TOPOLOGY: Linear ( i v ) ANTI-SENSE: Yes ( x i ) SEQUENCE DESCRIPTION: SEQ ID NO: 4:

CTCTCCACCG AGGAGCAGGC                                    20

( 2 ) INFORMATION FOR SEQ ID NO: 5:

( i ) SEQUENCE CHARACTERISTICS:
( A ) LENGTH: 20
( B ) TYPE: Nucleic Acid
( C ) STRANDEDNESS: Single
( D ) TOPOLOGY: Linear ( i v ) ANTI-SENSE: Yes ( x i ) SEQUENCE DESCRIPTION: SEQ ID NO: 5:

TGCCTTTCGC GGTCTCGCTC                                    20

( 2 ) INFORMATION FOR SEQ ID NO: 6:

( i ) SEQUENCE CHARACTERISTICS:
( A ) LENGTH: 20
( B ) TYPE: Nucleic Acid
( C ) STRANDEDNESS: Single
( D ) TOPOLOGY: Linear ( i v ) ANTI-SENSE: Yes ( x i ) SEQUENCE DESCRIPTION: SEQ ID NO: 6:

GGAACTGCCT TTCGCGGTCT                                    20

( 2 ) INFORMATION FOR SEQ ID NO: 7:

( i ) SEQUENCE CHARACTERISTICS:
( A ) LENGTH: 20
( B ) TYPE: Nucleic Acid
( C ) STRANDEDNESS: Single
( D ) TOPOLOGY: Linear ( i v ) ANTI-SENSE: Yes ( x i ) SEQUENCE DESCRIPTION: SEQ ID NO: 7:

TCGGCTCCTC CCGGCCGCGC 20

( 2 ) INFORMATION FOR SEQ ID NO: 8:

( i ) SEQUENCE CHARACTERISTICS:
        ( A ) LENGTH: 20
        ( B ) TYPE: Nucleic Acid
        ( C ) STRANDEDNESS: Single
        ( D ) TOPOLOGY: Linear ( i v ) ANTI-SENSE: Yes ( x i ) SEQUENCE DESCRIPTION: SEQ ID NO: 8:

CGCGCTCGGC TCCTCCCGGC 20

( 2 ) INFORMATION FOR SEQ ID NO: 9:

( i ) SEQUENCE CHARACTERISTICS:
        ( A ) LENGTH: 20
        ( B ) TYPE: Nucleic Acid
        ( C ) STRANDEDNESS: Single
        ( D ) TOPOLOGY: Linear ( i v ) ANTI-SENSE: Yes ( x i ) SEQUENCE DESCRIPTION: SEQ ID NO: 9:

CATTCCTGCC GCTCCCTGGG 20

( 2 ) INFORMATION FOR SEQ ID NO: 10:

( i ) SEQUENCE CHARACTERISTICS:
        ( A ) LENGTH: 20
        ( B ) TYPE: Nucleic Acid
        ( C ) STRANDEDNESS: Single
        ( D ) TOPOLOGY: Linear ( i v ) ANTI-SENSE: Yes ( x i ) SEQUENCE DESCRIPTION: SEQ ID NO: 10:

AGTGCTACGG TGCGGGCGCG 20

( 2 ) INFORMATION FOR SEQ ID NO: 11:

( i ) SEQUENCE CHARACTERISTICS:
        ( A ) LENGTH: 20
        ( B ) TYPE: Nucleic Acid
        ( C ) STRANDEDNESS: Single
        ( D ) TOPOLOGY: Linear ( i v ) ANTI-SENSE: Yes ( x i ) SEQUENCE DESCRIPTION: SEQ ID NO: 11:

CTTTCATATT CTTCTTGGAG 20

( 2 ) INFORMATION FOR SEQ ID NO: 12:

( i ) SEQUENCE CHARACTERISTICS:
        ( A ) LENGTH: 18
        ( B ) TYPE: Nucleic Acid
        ( C ) STRANDEDNESS: Single
        ( D ) TOPOLOGY: Linear ( i v ) ANTI-SENSE: Yes ( x i ) SEQUENCE DESCRIPTION: SEQ ID NO: 12:

TCTGAGTAAC ACTTTCAT 18

( 2 ) INFORMATION FOR SEQ ID NO: 13:

( i ) SEQUENCE CHARACTERISTICS:
        ( A ) LENGTH: 20
        ( B ) TYPE: Nucleic Acid
        ( C ) STRANDEDNESS: Single
        ( D ) TOPOLOGY: Linear ( i v ) ANTI-SENSE: Yes ( x i ) SEQUENCE DESCRIPTION: SEQ ID NO: 13:

TTGGACGGAC GGCCGTGGAG      20

( 2 ) INFORMATION FOR SEQ ID NO: 14:

( i ) SEQUENCE CHARACTERISTICS:
        ( A ) LENGTH: 20
        ( B ) TYPE: Nucleic Acid
        ( C ) STRANDEDNESS: Single
        ( D ) TOPOLOGY: Linear ( i v ) ANTI-SENSE: Yes ( x i ) SEQUENCE DESCRIPTION: SEQ ID NO: 14:

TCTTCAGAGG GTGCGTCTAC      20

( 2 ) INFORMATION FOR SEQ ID NO: 15:

( i ) SEQUENCE CHARACTERISTICS:
        ( A ) LENGTH: 20
        ( B ) TYPE: Nucleic Acid
        ( C ) STRANDEDNESS: Single
        ( D ) TOPOLOGY: Linear ( i v ) ANTI-SENSE: Yes ( x i ) SEQUENCE DESCRIPTION: SEQ ID NO: 15:

CTTGGAGAAG GCCTTGTCTT      20

( 2 ) INFORMATION FOR SEQ ID NO: 16:

( i ) SEQUENCE CHARACTERISTICS:
        ( A ) LENGTH: 20
        ( B ) TYPE: Nucleic Acid
        ( C ) STRANDEDNESS: Single
        ( D ) TOPOLOGY: Linear ( i v ) ANTI-SENSE: Yes ( x i ) SEQUENCE DESCRIPTION: SEQ ID NO: 16:

AGTAACACTT TCATATTCTT      20

( 2 ) INFORMATION FOR SEQ ID NO: 17:

( i ) SEQUENCE CHARACTERISTICS:
        ( A ) LENGTH: 20
        ( B ) TYPE: Nucleic Acid
        ( C ) STRANDEDNESS: Single
        ( D ) TOPOLOGY: Linear ( i v ) ANTI-SENSE: Yes ( x i ) SEQUENCE DESCRIPTION: SEQ ID NO: 17:

GAAACAAATA AGTCTGAGTA      20

( 2 ) INFORMATION FOR SEQ ID NO: 18:

( i ) SEQUENCE CHARACTERISTICS:
        ( A ) LENGTH: 20
        ( B ) TYPE: Nucleic Acid (C) STRANDEDNESS: Single
        (D) TOPOLOGY: Linear (iv) ANTI-SENSE: Yes (xi) SEQUENCE DESCRIPTION: SEQ ID NO: 18:

AGTCCTCCGT CTCCTGCAAC 20

(2) INFORMATION FOR SEQ ID NO: 19:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 19:

TACCCGAGAG GCACGTGAGC 20

(2) INFORMATION FOR SEQ ID NO: 20:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 20:

TCTGGCATTT TCTCATAGTC 20

(2) INFORMATION FOR SEQ ID NO: 21:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 21:

CCCTTCCATAA ATGAACAGC 20

(2) INFORMATION FOR SEQ ID NO: 22:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 22:

AACTTCTCCA TGCTACCCGA 20

(2) INFORMATION FOR SEQ ID NO: 23:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes ( x i ) SEQUENCE DESCRIPTION: SEQ ID NO: 23:

GCAACGCCAT AAGACAGGAG 20

( 2 ) INFORMATION FOR SEQ ID NO: 24:

( i ) SEQUENCE CHARACTERISTICS:
        ( A ) LENGTH: 20
        ( B ) TYPE: Nucleic Acid
        ( C ) STRANDEDNESS: Single
        ( D ) TOPOLOGY: Linear ( i v ) ANTI-SENSE: Yes ( x i ) SEQUENCE DESCRIPTION: SEQ ID NO: 24:

CATAACCTGG CCTGCAACGC 20

( 2 ) INFORMATION FOR SEQ ID NO: 25:

( i ) SEQUENCE CHARACTERISTICS:
        ( A ) LENGTH: 20
        ( B ) TYPE: Nucleic Acid
        ( C ) STRANDEDNESS: Single
        ( D ) TOPOLOGY: Linear ( i v ) ANTI-SENSE: Yes ( x i ) SEQUENCE DESCRIPTION: SEQ ID NO: 25:

CATTCCATGA ACTCTGCAAG 20

( 2 ) INFORMATION FOR SEQ ID NO: 26:

( i ) SEQUENCE CHARACTERISTICS:
        ( A ) LENGTH: 20
        ( B ) TYPE: Nucleic Acid
        ( C ) STRANDEDNESS: Single
        ( D ) TOPOLOGY: Linear ( i v ) ANTI-SENSE: Yes ( x i ) SEQUENCE DESCRIPTION: SEQ ID NO: 26:

TGGTGACCTC AGGGATAAAG 20

( 2 ) INFORMATION FOR SEQ ID NO: 27:

( i ) SEQUENCE CHARACTERISTICS:
        ( A ) LENGTH: 20
        ( B ) TYPE: Nucleic Acid
        ( C ) STRANDEDNESS: Single
        ( D ) TOPOLOGY: Linear ( i v ) ANTI-SENSE: Yes ( x i ) SEQUENCE DESCRIPTION: SEQ ID NO: 27:

CACTGCAACC TCCGTCTCCC 20

( 2 ) INFORMATION FOR SEQ ID NO: 28:

( i ) SEQUENCE CHARACTERISTICS:
        ( A ) LENGTH: 20
        ( B ) TYPE: Nucleic Acid
        ( C ) STRANDEDNESS: Single
        ( D ) TOPOLOGY: Linear ( i v ) ANTI-SENSE: Yes ( x i ) SEQUENCE DESCRIPTION: SEQ ID NO: 28:

CCCTTGGGCTG TGGATGACT 20

( 2 ) INFORMATION FOR SEQ ID NO: 29:

( i ) SEQUENCE CHARACTERISTICS:
    ( A ) LENGTH: 20
    ( B ) TYPE: Nucleic Acid
    ( C ) STRANDEDNESS: Single
    ( D ) TOPOLOGY: Linear ( i v ) ANTI-SENSE: Yes ( x i ) SEQUENCE DESCRIPTION: SEQ ID NO: 29:

GCGGGATGAC AGAAGAGCGG     20

( 2 ) INFORMATION FOR SEQ ID NO: 30:

( i ) SEQUENCE CHARACTERISTICS:
    ( A ) LENGTH: 20
    ( B ) TYPE: Nucleic Acid
    ( C ) STRANDEDNESS: Single
    ( D ) TOPOLOGY: Linear ( i v ) ANTI-SENSE: Yes ( x i ) SEQUENCE DESCRIPTION: SEQ ID NO: 30:

GCCACCACAG CCTCTCCCTC     20

( 2 ) INFORMATION FOR SEQ ID NO: 31:

( i ) SEQUENCE CHARACTERISTICS:
    ( A ) LENGTH: 20
    ( B ) TYPE: Nucleic Acid
    ( C ) STRANDEDNESS: Single
    ( D ) TOPOLOGY: Linear ( i v ) ANTI-SENSE: Yes ( x i ) SEQUENCE DESCRIPTION: SEQ ID NO: 31:

CGTGCCAGTG TGGAGTGAGG     20

( 2 ) INFORMATION FOR SEQ ID NO: 32:

( i ) SEQUENCE CHARACTERISTICS:
    ( A ) LENGTH: 20
    ( B ) TYPE: Nucleic Acid
    ( C ) STRANDEDNESS: Single
    ( D ) TOPOLOGY: Linear ( i v ) ANTI-SENSE: Yes ( x i ) SEQUENCE DESCRIPTION: SEQ ID NO: 32:

TGTGTCCTGC AATCGGTGGC     20

( 2 ) INFORMATION FOR SEQ ID NO: 33:

( i ) SEQUENCE CHARACTERISTICS:
    ( A ) LENGTH: 20
    ( B ) TYPE: Nucleic Acid
    ( C ) STRANDEDNESS: Single
    ( D ) TOPOLOGY: Linear ( i v ) ANTI-SENSE: Yes ( x i ) SEQUENCE DESCRIPTION: SEQ ID NO: 33:

GCAAAGCGGG CCCAGGAGAA     20

( 2 ) INFORMATION FOR SEQ ID NO: 34:

( i ) SEQUENCE CHARACTERISTICS:
    ( A ) LENGTH: 20
    ( B ) TYPE: Nucleic Acid (C) STRANDEDNESS: Single
            (D) TOPOLOGY: Linear (i v) ANTI-SENSE: Yes (x i) SEQUENCE DESCRIPTION: SEQ ID NO: 34:

CCTCCACCCA CGCTTATCCA 20

(2) INFORMATION FOR SEQ ID NO: 35:

(i) SEQUENCE CHARACTERISTICS:
            (A) LENGTH: 20
            (B) TYPE: Nucleic Acid
            (C) STRANDEDNESS: Single
            (D) TOPOLOGY: Linear (i v) ANTI-SENSE: Yes (x i) SEQUENCE DESCRIPTION: SEQ ID NO: 35:

AGTCAAAGGA AGTTCACGGG 20

(2) INFORMATION FOR SEQ ID NO: 36:

(i) SEQUENCE CHARACTERISTICS:
            (A) LENGTH: 20
            (B) TYPE: Nucleic Acid
            (C) STRANDEDNESS: Single
            (D) TOPOLOGY: Linear (i v) ANTI-SENSE: Yes (x i) SEQUENCE DESCRIPTION: SEQ ID NO: 36:

TGATCCGTGA TGCATGCTGT 20

(2) INFORMATION FOR SEQ ID NO: 37:

(i) SEQUENCE CHARACTERISTICS:
            (A) LENGTH: 20
            (B) TYPE: Nucleic Acid
            (C) STRANDEDNESS: Single
            (D) TOPOLOGY: Linear (i v) ANTI-SENSE: Yes (x i) SEQUENCE DESCRIPTION: SEQ ID NO: 37:

AGATGCCTTG CGTTGGCTGC 20

(2) INFORMATION FOR SEQ ID NO: 38:

(i) SEQUENCE CHARACTERISTICS:
            (A) LENGTH: 20
            (B) TYPE: Nucleic Acid
            (C) STRANDEDNESS: Single
            (D) TOPOLOGY: Linear (i v) ANTI-SENSE: Yes (x i) SEQUENCE DESCRIPTION: SEQ ID NO: 38:

CACTTAGCCG TGCGTTGGTG 20

(2) INFORMATION FOR SEQ ID NO: 39:

(i) SEQUENCE CHARACTERISTICS:
            (A) LENGTH: 20
            (B) TYPE: Nucleic Acid
            (C) STRANDEDNESS: Single
            (D) TOPOLOGY: Linear (i v) ANTI-SENSE: Yes ( x i ) SEQUENCE DESCRIPTION: SEQ ID NO: 39:

GTGGTTGCGT GCCGATTCAC 20

( 2 ) INFORMATION FOR SEQ ID NO: 40:

( i ) SEQUENCE CHARACTERISTICS:
        ( A ) LENGTH: 20
        ( B ) TYPE: Nucleic Acid
        ( C ) STRANDEDNESS: Single
        ( D ) TOPOLOGY: Linear ( i v ) ANTI-SENSE: Yes ( x i ) SEQUENCE DESCRIPTION: SEQ ID NO: 40:

UGUGUCCTGC AATCGGUGGC 20

( 2 ) INFORMATION FOR SEQ ID NO: 41:

( i ) SEQUENCE CHARACTERISTICS:
        ( A ) LENGTH: 20
        ( B ) TYPE: Nucleic Acid
        ( C ) STRANDEDNESS: Single
        ( D ) TOPOLOGY: Linear ( i v ) ANTI-SENSE: No ( x i ) SEQUENCE DESCRIPTION: SEQ ID NO: 41:

CTGGGATCCC ATCACCCTCC 20

( 2 ) INFORMATION FOR SEQ ID NO: 42:

( i ) SEQUENCE CHARACTERISTICS:
        ( A ) LENGTH: 21
        ( B ) TYPE: Nucleic Acid
        ( C ) STRANDEDNESS: Single
        ( D ) TOPOLOGY: Linear ( i v ) ANTI-SENSE: No ( x i ) SEQUENCE DESCRIPTION: SEQ ID NO: 42:

TGGGATCCCA AGTCTACTTC C 21

ANTISENSE COMPOSITIONS AND METHODS FOR MODULATING TYPE I INTERLEUKIN-1 RECEPTOR EXPRESSION

FIELD OF THE INVENTION

This invention relates to the design and synthesis of nuclease resistant oligomers that are complementary to and specifically hybridizable with nucleic acids encoding type I IL-1 receptor.

BACKGROUND OF THE INVENTION

Interleukin-1 (IL-1) is a polypeptide cytokine of 17.5 kDa. Two forms of IL-1 (IL-1α and IL-1β) are released from a variety of cells in response to inflammatory insult. IL-1α and IL-1β are a part of a complex network involved in mediating a wide range of immune responses. Dinarello, *Eur. Cytokine Netw.*, 5, 517 (1994); Dinarello, *The FASEB Journal*, 8, 1314 (1994); Sims and Dower, *Eur. Cytokine Netw.*, 5, 539 (1994). IL-1 exerts pleiotropic effects on host defenses via two kinds of receptor proteins. The larger protein, type I (80 kDa), is responsible for transducing IL-1 signals across the cell membrane, whereas the smaller protein, type II (68 kDa), functions as an apparent "decoy" protein which binds IL-1 but does not transduce a pro-inflammatory intracellular signal. Colota et al., *Science*, 261, 472 (1993); Sims et al., *Clin. Immunol. Immunopath.*, 72, 9 (1994); Sims and Dower, *Eur. Cytokine Netw.*, 5, 539 (1994). An additional member of the IL-1 receptor (IL-1r) family is the IL-1 receptor antagonist (IL-1Ra), which is a specific soluble antagonist of both IL-1α and IL-1β. IL-1Ra binds to both the IL-1 receptors (types I and II) with affinities similar to that with which it binds to IL-1α and IL-1β, but does not transduce a signal. Arend, *Adv. Immunol.*, 54, 167 (1993); Dayer and Burger, *Eur. Cytokine Netw.*, 5, 563 (1994).

The normal function of IL-1 is as an inflammatory cytokine producing multiple effects in the body. Although these functions are important in response to infection and injury, IL-1 expression and secretion can be deleterious when occurring at high concentrations or for extended periods of time. Sims et al., *Clin. Immunol. Immunopath.*, 72, 9 (1994); Dinarello, *Eur. Cytokine Netw.*, 5, 517 (1994); Dinarello, *Blood Purif.*, 11, 118 (1993); Dinarello and Wolff, *N. Engl. J. Med.*, 328, 106 (1993).

A number of different strategies have been employed in an attempt to inhibit IL-1 receptor-mediated effects in order to examine the specific role played by IL-1 in various disease processes. These include administration of antibodies targeting either the IL-1 receptor [Geiger et al., *Clin Exp. Rheumatol.*, 11, 515 (1993); McNamara et al., *J. Surgical Res.*, 54, 316 (1993)] or IL-1Ra [Arend, Adv. *Immunol.*, 54, 167 (1993); Dinarello and Thompson, *Immunol. Today*, 12, 404 (1991); Schotanus et al., *Endocrinology*, 133, 2461 (1994)].

Another approach to inhibiting the expression of IL-1r is by employing antisense oligonucleotides. Most conventional therapeutic agents exert their effect by interaction with and modulation of one or more targeted endogenous proteins. If this modulation could be effected by interaction with DNA and/or subsequent inhibition of mRNA expression, a dramatic reduction in the amount of therapeutic agent required to effect inhibition of the activity of the protein could be achieved. As this approach allows highly selective targeting of particular DNA or RNA sequences, another advantage of antisense oligonucleotides as inhibitors of protein expression is the specificity which may be achieved accompanied by a corresponding decrease in side effects resulting from such treatment.

However, some oligonucleotides are susceptible to enzymatic degradation by a variety of ubiquitous nucleases which may be intracellularly or extracellularly located. The efficacy of unmodified, "wild-type" oligonucleotides (i.e., those containing phosphodiester linkages and 2'-deoxy-erythro-pentofuranosyl sugar moieties) as therapeutic agents may be suboptimal because they are rapidly degraded by nucleases. Therefore, modification of oligonucleotides for conferring nuclease resistance on them has been a focus of research directed towards the development of oligonucleotide therapeutics and diagnostics. In addition to nuclease stability, the ability of an oligonucleotide to bind to a specific DNA or RNA with fidelity is a further important factor.

Oligonucleotides modified to exhibit resistance to nucleases and to hybridize with appropriate strength and fidelity to target DNA or RNA are greatly desired for use as research reagents, diagnostic agents and as oligonucleotide therapeutics. Various 2'-substitutions have been introduced in the sugar moiety of oligonucleotides. The nuclease resistance of these compounds has been increased by the introduction of 2'-substituents such as halo, alkoxy and allyloxy groups.

Ikehara et al. *Eur. J. Biochem.*, 139, 447 (1984) have reported the synthesis of a mixed octamer containing one 2'-deoxy-2'-fluoroguanosine residue or one 2'-deoxy-2'-fluoroadenine residue. Guschlbauer and Jankowski *Nucleic Acids Res.*, 8, 1421 (1980) have shown that the contribution of the 3'-endo increases with increasing electronegativity of the 2'-substituent. Thus, 2'-deoxy-2'-fluorouridine contains 85% of the C3'-endo conformer.

Ikehara et al. *Nucleic Acids Res.*, 4, 4249 (1978) have shown that a 2'-chloro or bromo substituent in poly(2'-deoxyadenylic acid) provides nuclease resistance. Eckstein et al. *Biochemistry*, 11, 4336 (1972) have reported that poly(2'-chloro-2'-deoxyuridylic acid) and poly(2'-chloro-2'-deoxycytidylic acid) are resistant to various nucleases. Inoue et al. have described the synthesis of mixed oligonucleotide sequences containing 2'-O-methyl substituents. The mixed 2'-O-methyl-substituted oligonucleotide hybridized to its RNA complement as strongly as the RNA-RNA duplex which is significantly stronger than the same sequence RNA-DNA heteroduplex ($T_m$s, 49.0 and 50.1 versus 33.0 degrees for nonamers). *Nucleic Acids Research*, 15, 6131 (1987). Shibahara et al. have reported the synthesis of mixed oligonucleotides containing 2'-O-methyl substituents which were designed to inhibit HIV replication. *Nucleic Acids Research*, 17, 239 (1987).

U.S. Pat. 5,013,830, issued May 7, 1991, discloses mixed oligonucleotides comprising an RNA portion, bearing 2'-O-alkyl substituents, conjugated to a DNA portion via a phosphodiester linkage. However, being phosphodiesters, these oligonucleotides are susceptible to nuclease cleavage.

European Patent application 339,842, filed Apr. 13, 1989, discloses 2'-O-substituted phosphorothioate oligonucleotides, including 2'-O-methylribooligonucleotide phosphorothioate derivatives. This application also discloses 2'-O-methyl phosphodiester oligonucleotides which lack nuclease resistance.

International Publication Number WO 91/06556, published May 16, 1991, discloses oligomers derivatized at the 2' position with substituents, which are stable to nuclease activity. Specific 2'-O-substituents which were incorporated into oligonucleotides include ethoxycarbonylmethyl (ester form), and its acid, amide and substituted amide forms.

European Patent application 399,330, filed May 15, 1990, discloses nucleotides having 2'-O-alkyl substituents.

International Publication Number WO 91/15499, published Oct. 17, 1991, discloses oligonucleotides bearing 2'-O-alkyl, -alkenyl and -alkynyl substituents.

U.S. Pat. No. 5,135,917, issued Aug. 4, 1992, discloses oligonucleotide compounds having 2'-deoxy sugar moieties which bind to mRNA coding for human IL-1 receptors. The oligomers of the present invention differ from the compounds described in this patent in that the oligomers disclosed in the present application comprise nucleosides bearing 2'-substituents on the sugar moieties. The 2'-substitution on sugar moieties makes oligomers of the invention nuclease resistant.

It has been recognized that nuclease resistance of oligonucleotides and fidelity of hybridization are of great importance in the development of oligonucleotide therapeutics. Oligonucleotides possessing nuclease resistance are also desired as research reagents and diagnostic agents.

SUMMARY OF THE INVENTION

In accordance with the present invention, nuclease resistant compositions which modulate expression of type I IL-1 receptor are provided. These compositions are comprised of sugar-modified oligomers which are specifically hybridizable with selected sequences of target DNA or RNA encoding type I IL-1 receptor.

The nuclease resistant oligomers of the present invention include a single strand of nucleosides connected via covalent linkages. In a preferred embodiment, the oligomer of the present invention is an "oligonucleotide" wherein the individual nucleosides of the oligonucleotide are connected via phosphorous linkages. Preferred phosphorous linkages include phosphodiester, phosphorothioate and phosphorodithioate linkages, with phosphodiester and phosphorothioate linkages being particularly preferred. An oligomer of the present invention also includes an "oligonucleoside," wherein the individual nucleosides of the oligonucleoside are connected via non-phosphorous linkages.

The oligomers of this invention may range from about 5 to about 50 nucleobases in length. However, in accordance with a preferred embodiment of this invention, a sequence of about 8 to 30 nucleobases is preferred.

Preferred nucleobases of the invention include adenine, guanine, cytosine, uracil, thymine, xanthine, hypoxanthine, 2-aminoadenine, 6-methyl, 2-propyl and other alkyladenines, 5-halouracil, 5-halocytosine, 6-azauracil, 6-azacytosine and 6-azathymine, pseudouracil, 4-thiouracil, 8-haloadenine, 8-aminoadenine, 8-thioadenine, 8-thiol alkyladenines, 8-hydroxyadenine and other 8-substituted adenines, 8-haloguanine, 8-aminoguanine, 8-thiol guanine, 8-thiol alkylguanine, 8-hydroxyguanine and other 8-substituted guanines, other aza and deazauracils, other aza and deazathymidines, other aza and deazacytosines, other aza and deazaadenines, other aza and deazaguanines, 5-trifluoromethyl uracil and 5-trifluorocytosine.

The nucleosides of the oligomers of the present invention comprise nucleobases linked to 2'-substituted-erythro-pentofuranosyl sugar moieties. In accordance with this invention, at least one of the nucleosides of the oligomers of the invention is a 2'-substituted-erythro-pentofuranosyl-β-nucleoside. A halo, alkoxy, alkoxyalkoxy, aminoalkoxy, alkyl, azido, or amino group may be added as the 2'-substituent. For example, F, CN, $CF_3$, $OCF_3$, OCN, O-alkyl (alkoxy), O-alkyl-O-alkyl (alkoxyalkoxy), S-alkyl, SMe, $SO_2Me$, $ONO_2$, $NO_2$, $N_3$, $NH_3$, $NH_2$, NH-alkyl, $OCH_2CH=CH_2$ (allyloxy), $OCH_3=CH_2$ or OCCH, where alkyl is a straight or branched chain of $C_1$ to $C_{20}$ with or without unsaturation within the carbon chain, may be added as 2'-substituents on the pentofuranosyl sugar moiety.

The present invention includes oligomers formed from a plurality of linked β-nucleosides including 2'-deoxy-erythro-pentofuranosyl-β-nucleosides. These nucleosides are connected by charged phosphorous linkages in a sequence that is complementary to or specifically hybridizable with a target DNA or RNA encoding type I IL-1r. The sequence of linked nucleosides is divided into at least two subsequences. The first subsequence includes β-nucleosides, having 2'-substituents, linked by charged phosphorous linkages. The second subsequence consists of 2'-deoxy-erythro-pentofuranosyl-β-nucleosides linked by charged phosphorous linkages bearing a negative charge at physiological pH. In further preferred embodiments there exists a third subsequence whose nucleosides are selected from those selectable for the first subsequence. In preferred embodiments the second subsequence is positioned between the first and third subsequences. Such oligomers of the present invention are also referred to as "chimeric" or "gapped" oligomers, or "chimeras."

The resulting novel oligomers of the invention are resistant to nuclease degradation and exhibit hybridization properties of higher quality relative to "wild-type" DNA-DNA, RNA-DNA and phosphorous-modified oligonucleotide duplexes.

The invention is also directed to methods for modulating type I IL-1r expression by an organism comprising contacting the organism with a composition formulated in accordance with the foregoing considerations. It is preferred that the target DNA or RNA portion be preselected to comprise that portion of DNA or RNA encoding type I IL-1r whose expression is to be modulated. Therefore, the oligomer to be employed is designed to be specifically hybridizable to the selected portion of target DNA or RNA.

This invention is also directed to methods of treating an organism having a disease characterized by the undesired expression of type I IL-1r. This method comprises contacting the organism with a composition in accordance with the foregoing considerations. The composition is preferably one which is designed to specifically bind to target DNA or RNA encoding type I IL-1r whose expression is to be inhibited.

The invention is also directed to methods for the selective binding of DNA or RNA encoding type I IL-1r for use as research reagents and diagnostic agents. Such selective and strong binding is accomplished by interacting such DNA or RNA with oligomers of the invention which are resistant to degradative nucleases and which display greater fidelity of hybridization relative to "wild-type" unmodified oligonucleotides.

BRIEF DESCRIPTION OF THE DRAWINGS

FIGS. 4A and 4B show flow cytometric analysis of the effect of ISIS 8807 on type I IL-1r protein expression in A549 cells.

A) Untreated cells and background fluorescence.

B) ISIS 8807 treated cells and background fluorescence.

Figure 5:
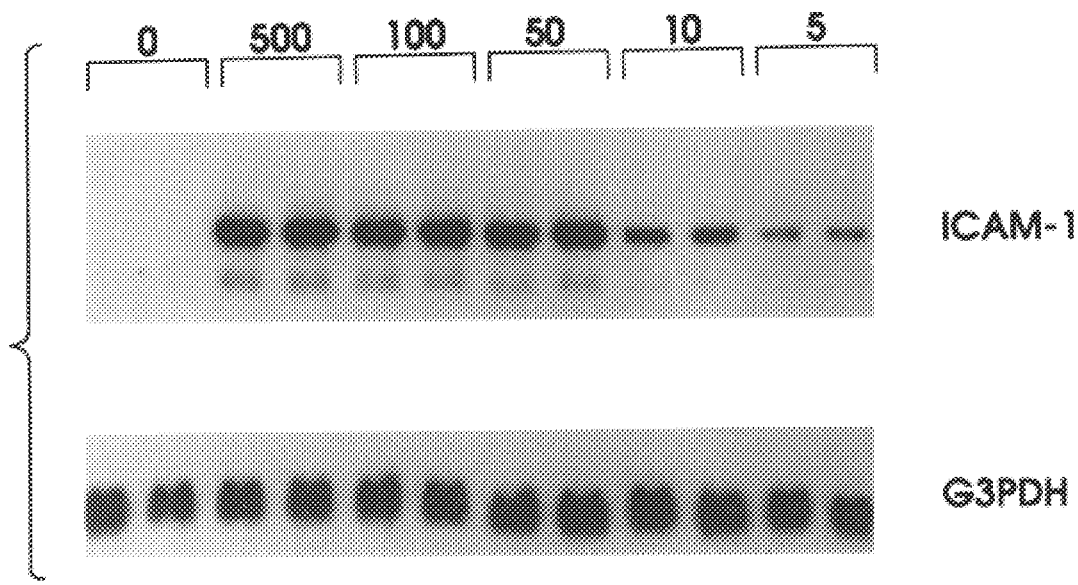

FIG. 5 is an autoradiogram showing dose response for the increase in ICAM-1 mRNA by IL-1α.

Figure 6:
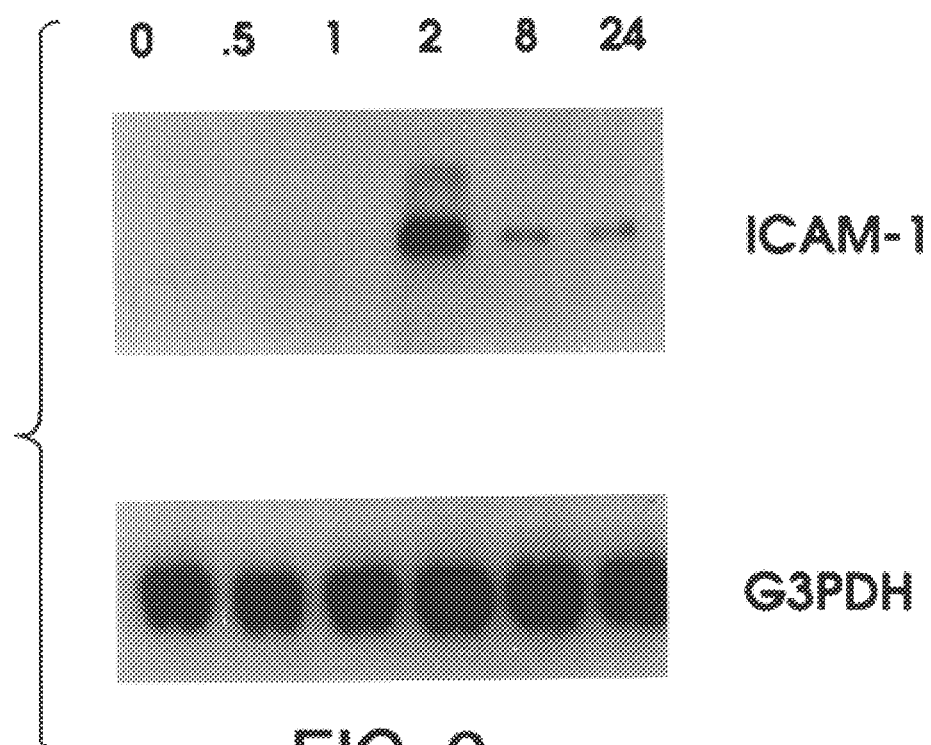

FIG. 6 is an autoradiogram showing time course of the increase in ICAM-1 mRNA by IL-1α.

Figure 7:
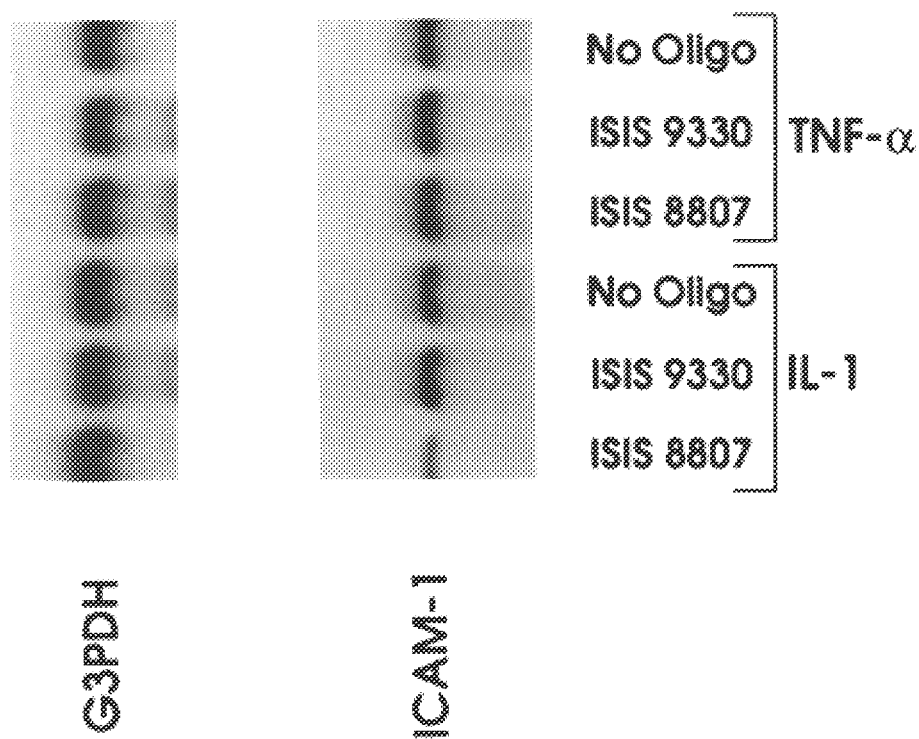

FIG. 7 is an autoradiogram showing the effect of ISIS 8807 and ISIS 9330 on the IL-1α and TNF-α induction of ICAM-1 mRNA.

DETAILED DESCRIPTION OF THE INVENTION

In accordance with the present invention, compositions that modulate DNA or RNA encoding type I IL-1 receptor (IL-1r) are provided. The compositions of the invention are resistant to nucleases and comprise a sugar-modified oligomer which is specifically hybridizable with a selected sequence of target DNA or RNA encoding type I IL-1r.

Oligonucleotides have become accepted as therapeutic moieties in the treatment of disease states in animals and man. For example, researchers in the field have now identified antisense, triplex and other oligonucleotide therapeutic compositions which are capable of modulating expression of genes implicated in viral, fungal and metabolic diseases.

U.S. Pat. No. 5,135,917 provides antisense oligonucleotides that inhibit human interleukin-1 receptor expression. U.S. Pat. No. 5,098,890 is directed to antisense oligonucleotide therapies for certain cancerous conditions. U.S. Pat. No. 5,087,617 provides methods for treating cancer patients with antisense oligonucleotides. U.S. Pat. No. 5,166,195 provides oligonucleotide inhibitors of HIV. U.S. Pat. No. 5,194,428 provides antisense oligonucleotides having antiviral activity against influenzavirus. U.S. Pat. No. 4,806,463 provides antisense oligonucleotides and methods using them to inhibit HTLV-III replication. U.S. Pat. Nos. 5,276,019 and 5,264,423 are directed to oligonucleotide analogs used to prevent replication of foreign nucleic acids in cells. U.S. Pat. No. 4,689,320 is directed to antisense oligonucleotides as antiviral agents specific to CMV. U.S. Pat. No. 5,242,906 provides antisense oligonucleotides useful in the treatment of latent EBV infections. Antisense oligonucleotides have been safely administered to humans and several clinical trials have either been completed or are underway. It is, thus, established that oligonucleotides can be useful therapeutic instrumentalities and that the same can be configured to be useful in treatment regimes for treatment of cells and animals, especially humans.

The oligonucleotides of the invention are conveniently synthesized using solid phase synthesis of known methodology, and are designed to be complementary to and/or specifically hybridizable with the preselected sequence of the target DNA or RNA encoding type I IL-1r. Nucleic acid synthesizers are commercially available and their use is understood by persons of ordinary skill in the art as being effective in generating any desired oligonucleotide of reasonable length.

In the context of this invention, the term "oligomer" refers to a plurality of nucleosides joined together via covalent linkages in a specific sequence from naturally and non-naturally occurring nucleobases, and includes oligonucleotides as well as oligonucleosides. "Oligonucleotides" refers to oligomers comprising a plurality of nucleosides joined together by phosphorous linkages. "Oligonucleosides" refers to oligomers comprising a plurality of nucleosides joined together by non-phosphorous linkages. Preferred nucleobases of the invention are joined through 2'-deoxy-erythro-pentofuranosyl and 2'-substituted-erythro-pentofuranosyl sugar moieties via phosphorous linkages, and include adenine, guanine, adenine, cytosine, uracil, thymine, xanthine, hypoxanthine, 2-aminoadenine, 6-methyl, 2-propyl and other alkyladenines, 5-halouracil, 5-halocytosine, 6-azauracil, 6-azacytosine and 6-azathymine, pseudouracil, 4-thiouracil, 8-haloadenine, 8-aminoadenine, 8-thioadenine, 8-thiol alkyladenine, 8-hydroxyadenine and other 8-substituted adenines, 8-haloguanine, 8-aminoguanine, 8-thioguanine, 8-thiol alkylguanine, 8-hydroxyguanine and other 8-substituted guanines, other aza and deazauracils, other aza and deazathymidines, other aza and deazacytosines, other aza and deazaadenines, other aza and deazaguanines, 5-trifluoromethyl uracil and 5-trifluorocytosine. The oligomers of the invention may also comprise modified nucleobases or nucleobases having other modifications consistent with the spirit of this invention, and in particular, modifications that increase their nuclease resistance in order to facilitate their use as therapeutic, diagnostic or research reagents.

In accordance with this invention at least one of the nucleosides of the oligomers of the invention is a 2'-substituted-erythro-pentofuranosyl-β-nucleoside. For example, the 2'-substituent may be F, CN, $CF_3$, $OCF_3$, OCN, O-alkyl (alkoxy), O-alkyl-O-alkyl (alkoxyalkoxy), S-alkyl, SMe, $SO_2Me$, $ONO_2$, $NO_2$, $N_3$, $NH_3$, $NH_2$, NH-alkyl, $OCH_3=CH_2$ or OCCH. In each of these, alkyl is a straight or branched chain of $C_1$ to $C_{20}$ with or devoid of unsaturation within the carbon chain.

A first preferred group of substituents includes 2'-fluoro substituents. A further preferred group of substituents includes O-alkyl and O-alkyl-O-alkyl substituents, wherein alkyl is a straight or branched chain of $C_1$–$C_{20}$. An additional preferred group of substituents includes cyano, fluoromethyl, thioalkoxyl, fluoroalkoxyl, alkylsulfinyl, alkylsulfonyl, allyloxy and alkeneoxy substituents.

The oligomers of the invention also include those that comprise nucleosides connected by charged phosphorous linkages, and whose sequences are divided into at least two subsequences. The first subsequence includes 2'-substituted-erythro-pentofuranosyl-β-nucleosides linked by phosphorous linkages. The second subsequence includes 2'-deoxy-erythro-pentofuranosyl-β-nucleosides linked by phosphorous linkages. In a preferred embodiment there exists a third subsequence whose nucleosides are selected from those selectable for the first subsequence, and the second subsequence is positioned between the first and the third subsequences. Preferred phosphorous linkages include phosphodiester, phosphorothioate and phosphorodithioate linkages. Such oligomers of the invention are known as "chimeras," or "chimeric" or "gapped" oligonucleotides.

In further embodiments, the oligomers of the present invention include oligonucleosides which comprise a plurality of nucleosides joined via non-phosphorous linkages that substitute for the internucleoside phosphorous linkages. In such compounds, the linkages include an —O—$CH_2$—$CH_2$—O— linkage (i.e., an ethylene glycol linkage) as well as other novel linkages disclosed in U.S. Pat. No. 5,223,618, issued Jun. 29, 1993, U.S. Pat. No. 5,378,825, issued Jan. 3, 1995 and International Publication No. WO 94/00467, published Jan. 6, 1994. Other modifications can be made to the sugar moiety, to the nucleobase, or to the phosphorous linkage, if present, of the nucleoside. Representative modifications are disclosed in International Publication Numbers WO 91/10671, published Jul. 25, 1991, WO 92/02258, published Feb. 20, 1992, WO 92/03568, published Mar. 5, 1992, and U.S. Pat. No. 5,138,045, issued Aug. 11, 1992.

It is preferred that the oligomers of the present invention be specifically hybridizable to the 5' untranslated region, 3' untranslated region, translation initiation site, 5' cap region, open reading frame, splice junction site, an exon or an intron.

It is preferred that the oligomers of the present invention be about 5 to about 50 nucleobases in length. It is more preferred that the oligomers of the invention be from about 8 to about 30 nucleobases in length.

Compositions of the present invention may be utilized as diagnostics, therapeutics and as research reagents. For therapeutics, an animal suspected of having a disease which can be treated by decreasing the expression of type I IL-1r is treated by administering oligomers in accordance with this invention. Oligomers of the invention can be utilized in pharmaceutical compositions by adding an effective amount of an oligomer of the invention to a pharmaceutically acceptable diluent or carrier.

The formulation of therapeutic compositions and their subsequent administration is believed to be within the skill of those in the art. In general, for therapeutics, a patient in need of such therapy is administered an oligomer in accordance with the invention, commonly in a pharmaceutically acceptable carrier, in doses ranging from 0.01 $\mu$g to 100 g per kg of body weight depending on the age of the patient and the severity of the disease state being treated. Further, the treatment may be a single dose or may be a regimen that may last for a period of time which will vary depending upon the nature of the disease being treated, its severity and the overall condition of the patient, and may extend from once daily to once every 20 years. Following treatment, the patient is monitored for changes in his/her condition and for alleviation of the symptoms of the disease state. The dosage of the oligomer may either be increased in the event the patient does not respond significantly to current dosage levels, or the dose may be decreased if an alleviation of the symptoms of the disease state is observed, or if the disease state has been ablated.

Dosing is dependent on severity and responsiveness of the disease being treated, with the course of treatment lasting from several days to several months, or until a cure is effected or a diminution of disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual oligomers, and can generally be estimated based on $EC_{50}$s found to be effective in in vitro and in vivo animal models. In general, dosage is from 0.01 $\mu$g to 100 g per kg of body weight, and may be given once or more daily, weekly, monthly or yearly, or even once every 2 to several years.

In some cases it may be more effective to treat a patient with an oligomer of the invention in conjunction with other therapeutic modalities. The dose of therapeutic agent to be administered and the route of administration may be adjusted according to the disease being treated and the severity of disease in the patient.

Following successful treatment, it may be desirable to have the patient undergo maintenance therapy to prevent the recurrence of the disease state, wherein the oligomer is administered in maintenance doses, ranging from 0.01 $\mu$g to 100 g per kg of body weight, once or more daily, to once every several years.

The pharmaceutical compositions of the present invention may be administered in a number of ways depending upon whether local or systemic treatment is desired and upon the area to be treated. Administration may be topical (including ophthalmic, vaginal, rectal, intranasal, transdermal), oral or parenteral. Parenteral administration includes intravenous drip, subcutaneous, intraperitoneal or intramuscular injection, or intrathecal or intraventricular administration.

Formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful.

Compositions for oral administration include powders or granules, suspensions or solutions in water or non-aqueous media, capsules, sachets or tablets. Thickeners, flavoring agents, diluents, emulsifiers, dispersing aids or binders may be desirable.

Compositions for intrathecal or intraventricular administration may include sterile aqueous solutions which may also contain buffers, diluents and other suitable additives.

Formulations for parenteral administration may include sterile aqueous solutions which may also contain buffers, diluents and other suitable additives.

The present invention is also suitable for detection of type I IL-1r overexpression in cell or tissue samples from patients who have a disease characterized by type I IL-1r overexpression. A number of assays may be formulated for the inhibition of type I IL-1r overexpression employing the present invention, which assays will commonly comprise contacting a cell or tissue sample with an oligomer of the invention under conditions selected to permit detection, and usually quantitation, of such inhibition. For example, radiolabeled oligomers can be prepared by $^{32}$P labeling at the 5' end with polynucleotide kinase. Sambrook et al., *Molecular Cloning. A Laboratory Manual,* Cold Spring Harbor Laboratory Press, 1989, Volume 2, pg. 10.59. Radiolabeled oligomers are then contacted with cell or tissue samples suspected of type I IL-1r expression or with RNA extracted from such samples. The sample is then washed to remove unbound oligomer. Radioactivity remaining in the sample indicates bound oligomer (which in turn indicates expression of the nucleic acids encoding type I IL-1r) and can be quantitated using a scintillation counter or other routine means. Comparison to appropriate controls allows expression of type I IL-1r to be determined. Radiolabeled oligomer can also be used to perform autoradiography of tissues to determine the localization, distribution and quantitation of type I IL-1r expression for research, diagnostic and therapeutic purposes. In such studies, tissue sections are treated with radiolabeled oligomer and washed as described above, then exposed to photographic emulsion according to routine autoradiography procedures. The emulsion, when developed, yields an image of silver grains over the regions expressing type I IL-1r. Quantitation of the silver grains permits IL-1r expression to be detected.

Analogous assays for fluorescent detection of type I IL-1r expression can be developed using oligomers of the invention which are conjugated with fluorescein or other fluorescent tag instead of radiolabeling. Such conjugations are routinely accomplished during solid phase synthesis using fluorescently-labeled amidites or CPG (e.g., fluorescein-labeled amidites or CPG available from Glen Research, Sterling, Va. See 1993 Catalog of Products for DNA Research, Glen Research, Sterling, Va., pg.21).

Each of these assay formats is known in the art. One of skill could easily adapt these known assays for detection of type I IL-1r expression in accordance with the teachings of the invention providing a novel and useful means to detect type I IL-1r expression.

In the context of the present invention, "contacting" cells or tissues with an oligomer means adding the oligomer, usually in a liquid carrier, to a cell suspension or tissue sample, either in vitro or ex vivo, or administering the oligomer to cells or tissues within an animal. "Modulating," as used herein, refers to either inhibition or stimulation. Inhibition of type I IL-1r expression is presently the preferred form of modulation.

The oligomers of this invention may also be used for research purposes. Thus, the specific hybridization exhibited by the oligomers may be used for assays, purifications, cellular product preparations and in other methodologies which may be appreciated by persons of ordinary skill in the art.

In the context of this invention, "hybridization" means hydrogen bonding, which may be Watson-Crick, Hoogsteen or reversed Hoogsteen hydrogen bonding, between complementary nucleobases. For example, adenine and thymine are complementary nucleobases which pair through the formation of hydrogen bonds. "Complementary," as used herein, also refers to sequence complementarity between two nucleic acid molecules. For example, if a nucleobase at a certain position of an oligomer is capable of hydrogen bonding with a nucleobase at the same position of a target DNA or RNA molecule, then the oligomer and the target DNA or RNA are considered to be complementary to each other at that position. The oligomer and the target DNA or RNA are complementary to each other when a sufficient number of corresponding positions in each molecule are occupied by nucleobases which can hydrogen bond with each other. Thus, "specifically hybridizable" and "complementary" are terms which are used to indicate a sufficient degree of complementarity such that stable and specific binding occurs between the oligomer and the target DNA or RNA. It is understood that an oligomer need not be 100% complementary to its target DNA or RNA sequence to be specifically hybridizable. An oligomer is specifically hybridizable when binding of the oligomer to the target DNA or RNA molecule interferes with the normal function of the target DNA or RNA to cause a loss of utility, and there is a sufficient degree of complementarity to avoid non-specific binding of the oligomer to non-target sequences under conditions in which specific binding is desired, i.e., under physiological conditions in the case of in vivo assays or therapeutic treatment, or in the case of in vitro assays, under conditions in which the assays are performed.

The relative ability of an oligomer to bind to complementary nucleic acids is compared by determining the melting temperature of a particular hybridization complex. The melting temperature ($T_m$), a characteristic physical property of double helices, is the temperature (in °C.) at which 50% helical versus coil (unhybridized) forms are present. $T_m$ is measured by using UV spectroscopy to determine the formation and breakdown (melting) of hybridization. Base stacking, which occurs during hybridization, is accompanied by a reduction in UV absorption (hypochromicity). Consequently, a reduction in UV absorption indicates a higher $T_m$. The higher the $T_m$, the greater the strength of the binding of the nucleic acid strands.

Several preferred embodiments of this invention are exemplified in accordance with the following nonlimiting examples.

EXAMPLES

Example 1

Oligonucleotide Synthesis

Oligonucleotides were synthesized and purified according to the method of Dean et al. *J. Biol. Chem.,* 269, 16416 (1994).

Example 2

Cell Culture and Oligonucleotide Treatment of Cells

Human lung carcinoma A549 and normal human dermal fibroblasts (NHDF) cell lines were obtained from American Type Culture Collection (Rockville, Md.). The cells were grown in DMEM containing 1 g of glucose/L and 10% FCS, and passaged routinely when 90–95% confluent. For oligonucleotide treatment, A549 and NHDF cells were grown in T-75 flasks and treated with the indicated concentration of oligonucleotide in the presence of 10 μg/mL of DOTMA/DOPE solution (LIPOFECTIN, Gibco-BRL, Grand Island, N.Y.) for 4 hours at 37° C. The solution was replaced with DMEM containing 10% FCS and the cells were allowed to recover for the indicated time at 37° C.

Example 3

Analysis of Type I IL-1 Receptor and ICAM-1 mRNA Levels

To obtain a human IL-1 receptor probe for use in Northern blotting, a two-step reverse transcriptase-polymerase chain reaction procedure was utilized. Chiang et al., *J. Biol. Chem.,* 266, 18162 (1991). Total cellular RNA was prepared by the guanidinium isothiocyanate method from human keratinocytes. Dean and McKay, *Proc. Natl. Acad. Sci.,* 91, 11762 (1994). First strand cDNA synthesis was accomplished by using avian myeloblastosis virus reverse transcriptase (Invitrogen, San Diego, Calif.). The PCR reaction was performed using primers hybridizing to produce a 846 base pair fragment corresponding to bases 190–1036 of the type I IL-1r cDNA (5' primer, 5'-CTGGGATCCCATCACCCTCC-3' (SEQ ID NO: 41); 3' primer, 5'-TGGGATCCCAAGTCTACTTCC-3' (SEQ ID NO: 42)). The identity of the fragment was confirmed by restriction analysis.

Single-stranded probe was generated through an asymmetric PCR reaction containing 50 nM each of dATP, dGTP and dTTP, 100 nM of the 3' primer, 25 ng of template DNA, [$^{32}$P] dCTP, 1.5 mM MgCl$_2$ and Taq polymerase (Promega, Madison, Wis.). The reaction was purified over a G-50 spin column (Boehringer Mannheim, Indianapolis, Ind.). A human ICAM-1 cDNA probe was radiolabeled by random prime. Chiang et al., *J. Biol. Chem.,* 266, 18162 (1991).

Total cellular RNA was isolated from oligonucleotide-treated cells by lysis with 4 M guanidinium isothiocyanate and purified by a cesium chloride gradient. Total RNA was resolved on 1% agarose gels containing 1.1% formaldehyde and then transferred to nylon membranes. Hybridization and quantitation of relative mRNA levels on a PhosphorImager were as described by Dean et al. *J. Biol. Chem.,* 269, 16416 (1994).

Example 4

Flow Cytometry

Expression of type I IL-1 receptor protein was determined by indirect immunofluorescence after oligonucleotide treatment as described in Example 3. Approximately 10$^6$ A549 cells were rinsed once with PBS and detached from the plate by incubation at 37° C. for 15 minutes in 2 mM EDTA/PBS without calcium and magnesium. After the addition of 2 mL PBS with calcium and magnesium, 1% FCS and 0.1% sodium azide, the cells were collected by centrifugation for 5 minutes at 1000 rpm. The cells were then incubated in the presence of a purified rat anti-human IL-1 receptor monoclonal antibody (PharMingen, San Diego, Calif.) for 1 hour at 4° C. After washing, the cells were incubated with 0.5 μg of biotinylated goat anti-rat Ig (PharMingen, San Diego, Calif.) for 30 minutes at 4° C. The cells were then washed and incubated with 0.1 μg of streptavidin-phycoerythrin for 30 minutes at 4° C. The cells were washed a final time and then resuspended in FACSflow (Becton Dickinson, San Jose, Calif.) with 0.5% formaldehyde before analysis on a FACSan flow cytometer (Becton Dickinson, San Jose, Calif.).

Example 5

Identification of an Antisense Oligonucleotide Inhibitor of IL-1 Receptor mRNA

Oligonucleotides which were predicted to hybridize to various regions of human type I IL-1r, including 5'-UTR, open reading frame and 3'-UTR, were synthesized and are shown in Tables 1 and 2.

TABLE 1

Activity of Phosphorothioate Oligonucleotides Targeting Human Type I IL-1 Receptor mRNA

| Oligo/Sequence (5'-3') | Activity* | mRNA target | SEQ ID NO |
|---|---|---|---|
| 8051 CCTCCAGGGCTGCGGCGGCT | — | 5' Cap | 1 |
| 8054 AGGGCTGCGGCGGCTCCACT | — | 5' Cap | 2 |
| 8055 CACCGAGGAGCAGGCGCGGC | — | 5' UTR | 3 |
| 8058 CTCTCCACCGAGGAGCAGGC | — | 5' UTR | 4 |
| 8059 TGCCTTTCGCGGTCTCGCTC | — | 5' UTR | 5 |
| 8061 GGAACTGCCTTTCGCGGTCT | — | 5' UTR | 6 |
| 8063 TCGGCTCCTCCCGGCCGCGC | — | 5' UTR | 7 |
| 8065 CGCGCTCGGCTCCTCCCGGC | — | 5' UTR | 8 |
| 7184 CATTCCTGCCGCTCCCTGGG | — | 5' UTR | 9 |
| 7185 AGTGCTACGGTGCGGGCGCG | — | 5' UTR | 10 |
| 7186 CTTTCATATTCTTCTTGGAG | — | AUG | 11 |
| 8716 TCTGAGTAACACTTTCAT | — | AUG | 12 |
| 8067 TTGGACGGACGGCCGTGGAG | — | sp jun/Ex1 | 13 |
| 8069 TCTTCAGAGGGTGCGTCTAC | — | sp jun/Ex2 | 14 |
| 8072 CTTGGAGAAGGCCTTGTCTT | — | sp jun/Ex2 | 15 |
| 8073 AGTAACACTTTCATATTCTT | — | sp jun/Ex3 | 16 |
| 7187 GAAACAAATAAGTCTGAGTA | — | ORF | 17 |
| 7188 AGTCCTCCGTCTCCTGCAAC | — | ORF | 18 |
| 7189 TACCCGAGAGGCACGTGAGC | — | ORF | 19 |
| 7727 TCTGGCATTTTCTCATAGTC | — | ORF | 20 |
| 7728 CCCTTCCATAAATGAACAGC | — | ORF | 21 |
| 7190 AACTTCTCCATGCTACCCGA | — | 3' UTR | 22 |
| 7191 GCAACGCCATAAGACAGGAG | — | 3' UTR | 23 |
| 7192 CATAACCTGGCCTGCAACGC | — | 3' UTR | 24 |
| 7193 CATTCCATGAACTCTGCAAG | — | 3' UTR | 25 |
| 7194 TGGTGACCTCAGGGATAAAG | — | 3' UTR | 26 |
| 8802 CACTGCAACCTCCGTCTCCC | 46 | 3' UTR | 27 |

TABLE 1-continued

Activity of Phosphorothioate Oligonucleotides Targeting Human Type I IL-1 Receptor mRNA

| Oligo/Sequence (5'-3') | Activity* | mRNA target | SEQ ID NO |
|---|---|---|---|
| 8803 CCCTTGGGCTGTGGATGACT | 70 | 3' UTR | 28 |
| 8804 GCGGGATGACAGAAGAGCGG | — | 3' UTR | 29 |
| 8805 GCCACCACAGCCTCTCCCTC | 58 | 3' UTR | 30 |
| 8806 CGTGCCAGTGTGGAGTGAGG | 77 | 3' UTR | 31 |
| 8807 TGTGTCCTGCAATCGGTGGC | 90 | 3' UTR | 32 |
| 8809 GCAAAGCGGGCCCAGGAGAA | 70 | 3' UTR | 33 |
| 8810 CCTCCACCCACGCTTATCCA | 71 | 3' UTR | 34 |
| 8811 AGTCAAAGGAAGTTCACGGG | — | 3' UTR | 35 |
| 8812 TGATCCGTGATGCATGCTGT | — | 3' UTR | 36 |
| 9330 AGATGCCTTGCGTTGGCTGC | — | 8807 control | 37 |
| 9331 CACTTAGCCGTGCGTTGGTG | — | 8807 control | 38 |
| 9332 GTGGTTGCGTGCCGATTCAC | — | 8807 control | 39 |

*Activity is expressed as % inhibition of type I IL-1r expression.
UTR = untranslated reGion; AUG = translation initiation site; ORF = open reading frame; sp jun = splice junction site.

The computer program OLIGO was used to predict the sequences which would have both a high $T_m$ and no self-complementarity. Rychlik and Rhoads, *Nucleic Acids Res.*, 17, 8543 (1989). Each of the oligonucleotides was evaluated for its ability to inhibit type I IL-1r mRNA expression in both A549 and NHDF cell lines at doses of 400 nM and 500 nM, respectively. It was found that both the cell lines expressed an mRNA transcript recognized by a radiolabeled type I IL-1r probe of approximately 5 kb, which is in agreement with previously published reports on the size of human type I IL-1r mRNA. Colota et al., *Science*, 261, 472 (1993). To facilitate uptake of the phosphorothioate oligonucleotides, cells were treated in the presence of 10 μg/mL of a cationic lipid formulation (DOTMA/DOPE). In A549 cells, oligonucleotides targeted to the 3'-UTR were found to decrease type I IL-1r mRNA expression (shown in Tables 1 and 2). The two most active oligonucleotides, ISIS 8806 (SEQ ID NO: 31) and ISIS 8807 (SEQ ID NO: 32), inhibited type I IL-1r mRNA expression by 77% and 90% of control, respectively. Also, in NHDF cells, ISIS 8806 and ISIS 8807 were most active and decreased type I IL-1r mRNA expression by 67% and 83% of control, respectively. These sequences are preferred. Table 2 shows the gapped phosphodiester and phosphorothioate oligonucleotides bearing 2' substituents that were synthesized and their activity expressed as % inhibition of type I IL-1r expression. All oligonucleotides shown in Table 2 are preferred.

TABLE 2

Gapped Oligonucleotides Targeting Human Type I IL-1 Receptor mRNA

| Oligo | Sequence (5'-3') | SEQ ID NO | Activity |
|---|---|---|---|
| 9410 | UsGsUsGsUsC sCsTsGsCsAsAsTsCsGsGsUsGsG sC (#) | 40 | 83 |
| 9411 | UoGoUoGoUoCoCsTsGsCsAsAsTsCsGoGoUoGoGoC (#) | 40 | <70 |
| 9579 | UsGsUsGsUsCsCsTsGsCsAsAsTsCsGsGsUsGsGsC (^) | 40 | 82 |
| 9580 | UoGoUoGoUoCoCsTsGsCsAsAsTsCsGoGoUoGoGoC (^) | 40 | 88 |
| 9624 | TsGsTsGsTsCsCsTsGsCsAsAsTsCsGsGsTsGsGsC (*) | 32 | 81 |

TABLE 2-continued

Gapped Oligonucleotides Targeting
Human Type I IL-1 Receptor mRNA

| Oligo | Sequence (5'-3') | SEQ ID NO | Activity |
|---|---|---|---|
| 9625 | ToGoToGoToCoCsTsGsCsAsAsTsCsGoGoToGoGoC (*) | 32 | <70 |
| 10298 | UsGsUsGsUsCsCsTsGsCsAsAsTsCsGsGsUsGsGsC (+) | 40 | 89 |

*Activity expressed as % inhibition of type I IL-1r mRNA expression.
o = P=O linkage
s = P=S linkage
Bold = 2'-substituted nucleobase
\# = 2'-O-propyl
^ = 2'-O-pentyl
* = 2'-O-methoxyethoxy
+ = 2'-fluoro

Example 6

Characterization of Inhibition of Type I IL-1r Receptor mRNA Expression

Figure 1:
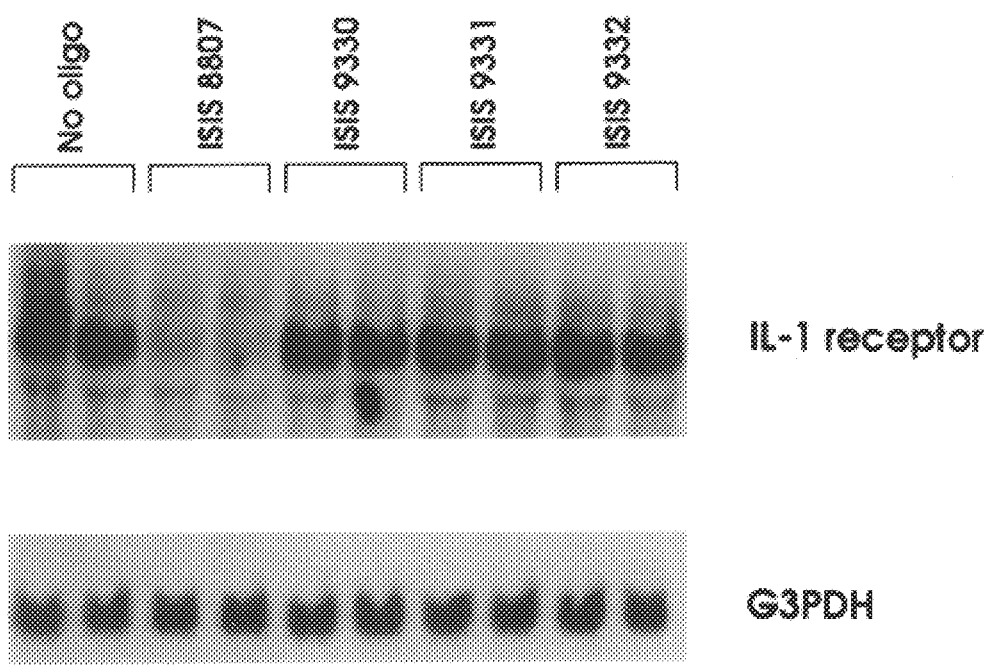
FIG. 1 is an autoradiogram showing the effect of ISIS 8807 and control oligonucleotides (ISIS 9330, ISIS 9331 and ISIS 9332) on type I IL-1r mRNA expression in A549 cells.

The cellular pharmacology of ISIS 8807 was further characterized. Three additional oligonucleotides, ISIS 9330, ISIS 9331 and ISIS 9332, were synthesized as controls, to demonstrate that the inhibition of type I IL-1r mRNA expression observed was oligonucleotide sequence specific. The control oligonucleotides retained the same nucleotide composition as ISIS 8807, but were randomized (scrambled controls, as shown in Table 1). A549 cells were treated with 400 nM of antisense oligonucleotides in duplicate for 4 hours in the presence of 10 µg/mL DOTMA/DOPE, washed and allowed to recover for an additional 20 hours. Total mRNA was extracted, resolved on 1% agarose gel and type I IL-1r mRNA expression determined. The blots were stripped and reprobed to determine expression levels of G3PDH. The control oligonucleotides were without effect on type I IL-1r mRNA expression in A549 cells at a concentration of 500 nM (FIG. 1). By contrast, ISIS 8807 decreased type I IL-1r mRNA expression by greater than 90%. The specificity of ISIS 8807 towards type I IL-1r mRNA was determined by stripping the IL-1r probed blot and reprobing for the housekeeping gene for glyceraldehyde-3-phosphate dehydrogenase (G3PDH). The level of expression of this gene was not affected by any of the oligonucleotides (FIG. 1).

Example 7

Dose Response for the Reduction of Type I IL-1r mRNA Expression

Figure 2A:
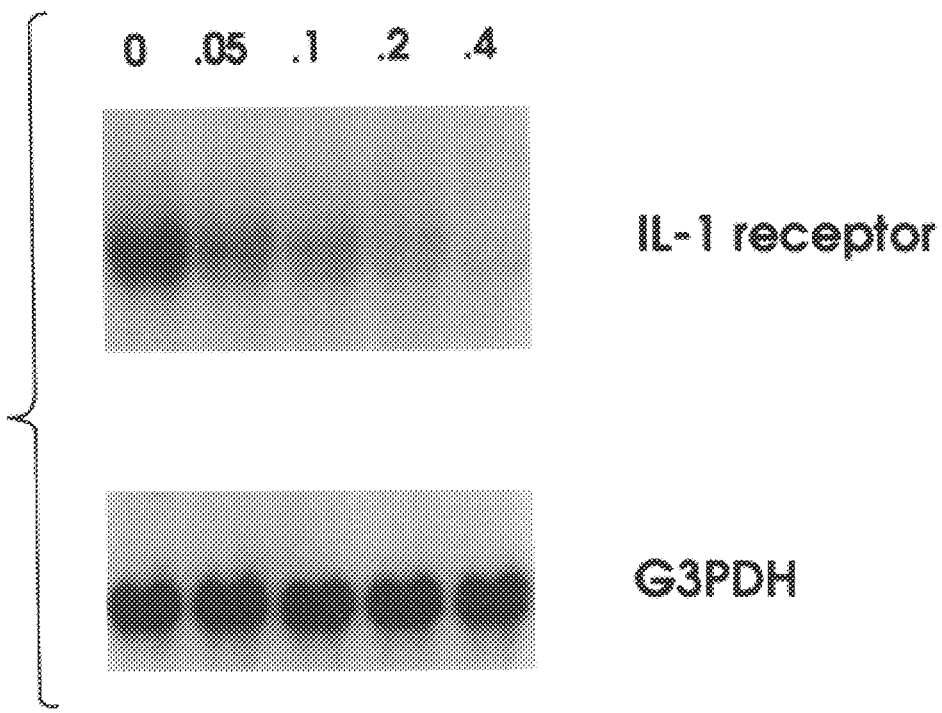
FIGS. 2(a) and 2(b) are autoradiograms showing dose response for the reduction in type I IL-1r mRNA expression by ISIS 8807 in A549 cells and normal human dermal fibroblasts, respectively.
Figure 2B:
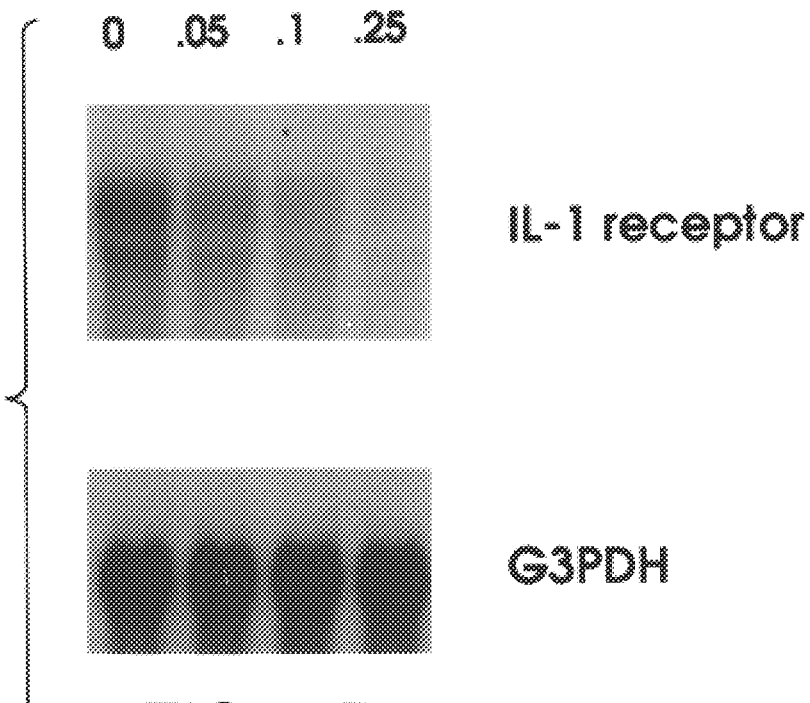

A549 cells or normal human dermal fibroblasts were treated with either 0, 0.05, 0.1, 0.2 and 0.4 µM or 0, 0.05, 0.1 and 0.25 µM, respectively, of ISIS 8807 for 4 hours in the presence of 10 µg/mL of DOTMA/DOPE, washed and allowed to recover for an additional 20 hours. Total mRNA was extracted, resolved on 1% agarose gel and type I IL-1r mRNA expression determined. The blots were stripped and reprobed to determine expression levels of G3PDH. Inhibition of type I IL-1r mRNA expression by ISIS 8807 was dose-dependent in A549 and NHDF cell lines. As observed in FIG. 2(a), in the A549 cell line, maximal reduction of type I IL-1r mRNA levels was achieved at 400 nM, with an $IC_{50}$ of 75 nM. As observed in FIG. 2(b), in the NHDF cell line, the $IC_{50}$ for ISIS 8807-dependent reduction in mRNA expression was approximately 100 nM.

Example 8

Kinetic Analysis of the Reduction of Type I IL-1r mRNA Expression

Figure 3:
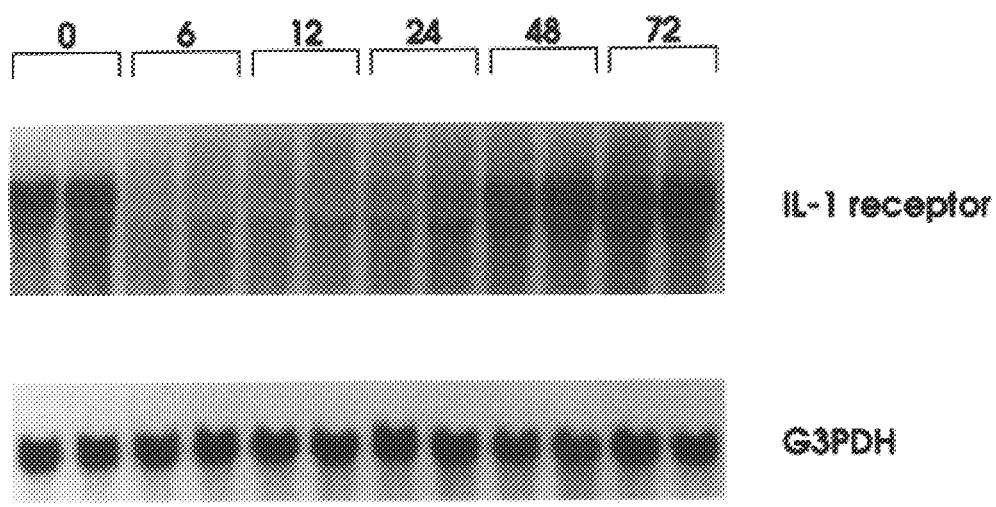
FIG. 3 is an autoradiogram showing kinetic analysis of the reduction in type I IL-1r mRNA expression by ISIS 8807.

To characterize the kinetics of oligonucleotide-dependent type I IL-1r mRNA inhibition, A549 cells were treated with 400 nM of ISIS 8807 in duplicate for 6, 24, 48 and 72 hours. The first 4 hours of treatment were in the presence of 10 µg/mL of DOTMA/DOPE. Total mRNA was extracted, resolved on 1% agarose gel and type I IL-1r mRNA expression determined. Type I IL-1r mRNA expression was reduced to 4% of control after 6 hours and to 9% of control after 12 hours (FIG. 3). After 24 hours, the mRNA levels began to recover, reaching 19% of control. Type I IL-1r mRNA levels increased steadily, reaching 72% of control at 72 hours after oligonucleotide treatment (FIG. 3).

Example 9

Inhibition of Type I IL-1r Receptor Expression

Type I IL-1r receptor protein expression was determined by flow cytometry. A549 cells were treated with 300 nM of an oligonucleotide (antisense or control) as described in Example 6. Expression of type I IL-1r protein was determined by flow cytometry. After 24 hours, ISIS 8807 decreased type I IL-1r protein expression to 40% of control (saline treated, FIG. 4), while ISIS 9332 (control oligonucleotide) had no effect on type I IL-1r protein expression.

Example 10

Dose Response for Increase in ICAM-1 mRNA by IL-1α

The effect of ISIS 8807 on the expression of an IL-1-dependent gene was examined in order to determine if the decrease in IL-1 receptor protein expression leads to a diminished cellular response to IL-1. A549 cells were treated in duplicate with 5, 10, 50, 100 and 500 pg/mL of IL-1α for 2 hours and then total mRNA was prepared and ICAM-1 expression determined. The blot was stripped and reprobed to determine expression levels of G3PDH. Basal levels of ICAM-1 mRNA were undetectable in A549 cells, but the levels could be dramatically increased by IL-1α treatment (FIG. 5). This increase in ICAM-1 mRNA expression was concentration-dependent, with an $IC_{50}$ of approximately 10 pg/mL (FIG. 5).

Example 11

Time Course for Increase in ICAM-1 mRNA by IL-1α

A549 cells were treated with 50 pg/mL of IL-1 for 0.5, 1, 2, 8 and 24 hours, and then total mRNA was prepared and ICAM-1 expression determined. The blot was stripped and reprobed to determine expression levels of G3PDH. ICAM-1 mRNA expression was maximal 2 hours after the addition of IL-1α to the cells and remained elevated for up to 24 hours (FIG. 6). Maximal reduction in type I IL-1r mRNA expression occurred between 6 and 24 hours after treatment with ISIS 8807, and this resulted in a decrease in type I IL-1 receptor protein expression of 60% at 24 hours.

Example 12

Effect of ISIS 8807 and ISIS 9330 on IL-1α and TNF-α Induction on ICAM-1 mRNA

A549 cells were treated with no oligonucleotide, ISIS 8807 or ISIS 9330 (scrambled control oligonucleotide) for 24 hours. Cells were then treated with 50 pg/mL of IL-1α or 50 pg/mL of TNF-α for 2 hours. Total mRNA was prepared and ICAM-1 expression determined. The blot was stripped and reprobed to determine expression levels of G3PDH. The reduction in type I IL-1r mRNA expression resulted in a 66% decrease in the IL-1α-dependent induction of ICAM-1 when compared to either a saline control or a scrambled oligonucleotide (ISIS 9330, FIG. 7). The reduction in ICAM-1 induction by ISIS 8807 was selective for IL-1α-mediated signaling as the oligonucleotide did not attenuate TNF-α-mediated ICAM-1 expression (FIG. 7).

Example 13

Diagnostics and Detection of Type I IL-1r Expression

Detection of IL-1r expression is useful diagnostically because IL-1r expression occurring at high concentrations and for extended periods of time can be deleterious. Sims et al., *Clin. Immunol. Immunopath.*, 72, 9 (1994); Dinarello, *Eur. Cytokine Netw.*, 5, 517 (1994); Dinarello, *Blood Purif.*, 11, 118 (1993); Dinarello and Wolff, *N. Engl. J. Med.*, 328, 106 (1993). Oligonucleotides are radiolabeled after synthesis by $^{32}$P labeling at the 5' end with polynucleotide kinase. Sambrook et al., *"Molecular Cloning. A Laboratory Manual,"* Cold Spring Harbor Laboratory Press, 1989, Volume 2, pg. 11.31–11.32. Radiolabeled oligonucleotide is contacted with tissue or cell samples (of a disease state) suspected of type I IL-1r expression under conditions whereby specific hybridization can occur, and the sample is washed to remove unbound oligonucleotide. A similar control is maintained wherein the radiolabeled oligonucleotide is contacted with a normal cell or tissue sample under conditions that allow specific hybridization, and the sample is washed to remove unbound oligonucleotide. Radioactivity remaining in the sample indicates bound oligonucleotide and is quantitated using a scintillation counter or other routine means. Comparison of the radioactivity remaining in the samples from normal and disease cells indicates expression of type I IL-1r.

Radiolabeled oligonucleotides of the invention are also useful in autoradiography. Tissue sections are treated with radiolabeled oligonucleotide and washed as described above, then exposed to photographic emulsion according to standard autoradiography procedures. A control with normal cell or tissue sample is also maintained. The emulsion, when developed, yields an image of silver grains over the regions expressing type I IL-1r, which is quantitated. The extent of type I IL-1r expression is determined by comparison of the silver grains observed with normal and disease cells.

Analogous assays for fluorescent detection of type I IL-1r expression use oligonucleotides of the invention which are labeled with fluorescein or other fluorescent tags. Labeled oligonucleotides are synthesized on an automated nucleic acid synthesizer (Applied Biosystems model 380B) using standard phosphoramidite chemistry with oxidation by iodine. β-cyanoethyldiisopropyl phosphoramidites are purchased from Applied Biosystems (Foster City, Calif.). Fluorescein-labeled amidites are purchased from Glen Research (Sterling, Va.). Incubation of oligonucleotide and biological sample is carried out as described for radiolabeled oligonucleotides except that instead of a scintillation counter, a fluorescence microscope is used to detect the fluorescence. Comparison of the fluorescence observed in samples from normal and disease cells indicates and can be used to quantitate type I IL-1r expression.

What is claimed is:

1. An oligomer comprising nucleosides, connected via covalent linkages, consisting of SEQ ID NO: 27, 28, 30–34 or 40 wherein at least one of said nucleosides bears a 2'-substituent.

2. The oligomer of claim 1 wherein said 2'-substituent is 2'-O-alkyl, 2'-O-alkyl-O-alkyl or 2'-fluoro.

3. The oligomer of claim 1 wherein at least one of said covalent linkages is a phosphodiester linkage.

4. The oligomer of claim 1 wherein at least one of said covalent linkages is a phosphorothioate linkage.

5. The oligomer of claim 1 comprising SEQ ID NO: 31, SEQ ID NO: 32 or SEQ ID NO: 40.

6. The oligomer of claim 5 wherein all of said nucleosides bear a 2'-H substituent.

7. An oligomer comprising nucleosides, connected via covalent linkages, consisting of SEQ ID NO: 27, 28, 30–34 or 40, said oligomer comprising a first subsequence and a second subsequence, wherein:

said first subsequence has at least one nucleoside bearing a 2'-substituent; and said second subsequence comprises 2'-deoxy-erythro-pentofuranosyl-β-nucleosides.

8. The oligomer of claim 7 wherein said 2'-substituent is 2'-O-alkyl, 2'-O-alkyl-O-alkyl or 2'-fluoro.

9. The oligomer of claim 7 wherein at least one of said covalent linkages is a phosphodiester linkage.

10. The oligomer of claim 7 wherein at least one of said covalent linkages is a phosphorothioate linkage.

11. The oligomer of claim 7 further comprising a third subsequence having at least one nucleoside bearing a 2'-substituent wherein said second subsequence is positioned between said first subsequence and said third subsequence.

12. The oligomer of claim 11 wherein said 2'-substituent is 2'-O-alkyl, 2'-O-alkyl-O-alkyl or 2'-fluoro.

13. The oligomer of claim 11 wherein said nucleosides of said first and third subsequences are connected via phosphodiester linkages and said nucleosides of said second subsequence are connected via phosphorothioate linkages.

14. The oligomer of claim 11 wherein said nucleosides of said first and third subsequences are connected via phosphorothioate linkages and said nucleosides of said second subsequence are connected via phosphodiester linkages.

15. The oligomer of claim 7 comprising a third subsequence having 2'-deoxy-erythro-pentofuranosyl-β-nucleosides wherein said first subsequence is positioned between said second subsequence and said third subsequence.

16. The oligomer of claim 15 wherein said 2'-substituent is 2'-O-alkyl, 2'-O-alkyl-O-alkyl or 2'-fluoro.

17. The oligomer of claim 15 wherein said nucleosides of said first and third subsequences are connected via phosphodiester linkages and said nucleosides of said second subsequence are connected via phosphorothioate linkages.

18. The oligomer of claim 15 wherein said nucleosides of said first and third subsequences are connected via phosphorothioate linkages and said nucleosides of said second subsequence are connected via phosphodiester linkages.

19. A method of modulating the expression of type I interleukin-1 receptor in a cell or tissue in vitro comprising contacting the cell or tissue with an oligomer specifically hybridizable with DNA or RNA encoding type I interleukin-1 receptor, said oligomer comprising nucleosides, connected via covalent linkages, consisting of SEQ ID NO: 27, 28, 30–34 or 40 wherein at least one of said nucleosides bears a 2'-substituent.

20. The method of claim 19 wherein said 2'-substituent is 2'-O-alkyl, 2'-O-alkyl-O-alkyl or 2'-fluoro.

21. The method of claim 19 wherein at least one of said covalent linkages is a phosphodiester linkage.

22. The method of claim 19 wherein at least one of said covalent linkages is a phosphorothioate linkage.

23. The method of claim 19 wherein said oligomer comprises SEQ ID NO: 31, SEQ ID NO: 32 or SEQ ID NO: 40.

24. The method of claim 23 wherein all of said nucleosides of said oligomer bear a 2'-H substituent.

25. A method of modulating the expression of type I interleukin-1 receptor in a cell or tissue in vitro comprising contacting the cell or tissue with an oligomer specifically hybridizable with DNA or RNA encoding type I interleukin-1 receptor, said oligomer comprising nucleosides, connected via covalent linkages, consisting of SEQ ID NO: 27, 28, 30–34 or 40, said oligomer comprising a first subsequence and a second subsequence, wherein:

said first subsequence has at least one nucleoside bearing a 2'-substituent; and said second subsequence has nucleosides comprising 2'-deoxy-erythro-pentofuranosyl-β-nucleosides.

26. The method of claim 25 wherein said 2'-substituent is 2'-O-alkyl, 2'-O-alkyl-O-alkyl or 2'-fluoro.

27. The method of claim 25 wherein at least one of said covalent linkages is a phosphodiester linkage.

28. The method of claim 25 wherein at least one of said covalent linkages is a phosphorothioate linkage.

29. The method of claim 25 wherein said oligomer comprises SEQ ID NO: 31, SEQ ID NO: 32 or SEQ ID NO: 40.

* * * * *

UNITED STATES PATENT AND TRADEMARK OFFICE
CERTIFICATE OF CORRECTION

PATENT NO. : 5,856,099
DATED : January 5, 1999
INVENTOR(S) : Miraglia, et al.

It is certified that error appears in the above-indentified patent and that said Letters Patent is hereby corrected as shown below:

At col 12, in Table 2, at Oligo Sequence 9410, please delete "UsGsUsGsUsCsCsTsGsCsAsAsTsCsGsGsUsGsGsC" and insert therefor --UsGsUsGsUsCsCsTsGsCsAsAsTsCsGsGsUsGsGsC--.

At col 12, in Table 2, at Oligo Sequence 9580, please delete "UoGoUcGoUoCoCsTsGsCsAsAsTsCsGoGoUoGoGoC" and insert therefor --UoGoUcGoUoCoCsTsGsCsAsAsTsCsGoGoUoGoGoC--.

In claim 11, line 50-51, please delete "subseqeuence" and insert therefor --subsequence--.

Signed and Sealed this

Seventeenth Day of August, 1999

Attest:

Q. TODD DICKINSON

Attesting Officer

Acting Commissioner of Patents and Trademarks